United States Patent
Bell et al.

(10) Patent No.: US 6,289,889 B1
(45) Date of Patent: Sep. 18, 2001

(54) SELF-HEATING FLEXIBLE PACKAGE

(75) Inventors: William L. Bell, Boulder; James L. Dippo, Arvada, both of CO (US)

(73) Assignee: TDA Research, Inc., Wheat Ridge, CO (US)

( * ) Notice: Subject to any disclaimer, the term of this patent is extended or adjusted under 35 U.S.C. 154(b) by 0 days.

(21) Appl. No.: 09/351,578

(22) Filed: Jul. 12, 1999

(51) Int. Cl.[7] .................................................. F24J 1/00

(52) U.S. Cl. ............................ 126/263.07; 126/263.08; 126/263.1; 252/70

(58) Field of Search ........... 126/263.01, 263.03–263.09, 126/262, 263.1; 252/70, 71; 426/107

(56) References Cited

U.S. PATENT DOCUMENTS

| | | |
|---|---|---|
| 3,079,911 | 3/1963 | Ryan et al. |
| 3,101,707 | 8/1963 | Ryan et al. |
| 3,288,217 | 11/1966 | Ralston ............................ 166/279 |
| 3,378,333 | 4/1968 | Brite ................................ 21/110 |
| 3,429,672 | 2/1969 | Young .............................. 44/3 |
| 3,512,516 * | 5/1970 | Glass et al. ...................... 126/263.07 |
| 3,535,246 | 10/1970 | Crowell ........................... 252/70 |

(List continued on next page.)

FOREIGN PATENT DOCUMENTS

| | | |
|---|---|---|
| 0017468 | 10/1980 | (EP) . |
| 0 564 680 A1 | 4/1992 | (EP) . |
| 2 089 970 A | 6/1982 | (GB) . |
| 56-76482 | 6/1981 | (JP) . |
| 56-135585 | 10/1981 | (JP) . |
| 4-73020 | 9/1992 | (JP) . |
| 87/00409 | 1/1987 | (WO) . |
| WO 91/10102 * | 7/1991 | (WO) ........................ 126/263.07 |
| 94/05136 | 3/1994 | (WO) . |
| 98/05906 | 2/1998 | (WO) . |

OTHER PUBLICATIONS

Military specification MIL–R–44398A (Jul. 1990) pp. 47–61.

Lane, G.A. (ed.) (1983) Solar Heat Storage: Latent Heat Materials. vol. I: Background and Scientific Principles, CRC Press, Inc., Boca Raton, FL, pp. 18–25, 30–39, 42–49, 54–55.

Sacharow, S. (Sep. 1988), "A hot and cold issue: Self–heating, self–chilling packages," Prepared Foods, pp. 98 and 101.

DST–1810P–487–86–vol. 9–NO1 (Mar. 18, 1986), pp. 43–44.

Military Specification MIL–R–44398A (Jul. 1990), pp. 47–61.

Chem Abstract 116:258459, "Effect of surfactants on the crystallization of Calcium Phosphate in the Calcium Oxide–Phosphorous Pentoxide–Water System," Kir'yanova et al., 1991.

Primary Examiner—James C. Yeung
(74) Attorney, Agent, or Firm—Greenlee, Winner and Sullivan, P.C.

(57) ABSTRACT

Improved heaters and self-heating packages that function without application of external energy. Heat is generated by contact of a heat-producing composition, such as calcium oxide, and an activating solution which is typically water. The heater contains multi-compartments containing heat-producing composition and activating solution. The heater is activated by application of hand pressure to rupture a frangible seal which allows the heater components to mix. The heater compartments are at least in part formed from flexible walls. The self-heating package has one or more products or product containers in thermal contact with one or more heaters. In preferred packaging embodiments, the heating package has one or more product containers or pouches in thermal contact with one or more heaters. In a specific embodiment, the product container is integrally formed with the heater. Preferred self-heating packages are constructed entirely of flexible packaging materials.

31 Claims, 9 Drawing Sheets

U.S. PATENT DOCUMENTS

| | | | |
|---|---|---|---|
| 3,550,578 | 12/1970 | Fearon et al. | 126/263 |
| 3,585,982 | 6/1971 | Hollinshead | 126/263 |
| 3,683,889 * | 8/1972 | Hoffman | 126/262 |
| 3,685,507 * | 8/1972 | Donnelly | 126/262 |
| 3,766,079 | 10/1973 | Jackman et al. | 252/188.3 R |
| 3,804,077 | 4/1974 | Williams | 126/263 |
| 3,903,011 | 9/1975 | Donnelly | 252/188.3 R |
| 4,057,047 | 11/1977 | Gossett | 126/263 |
| 4,067,313 | 1/1978 | Donnelly | 126/263 |
| 4,287,076 | 9/1981 | Babin et al. | 252/70 |
| 4,501,259 | 2/1985 | Apellaniz | 126/263 |
| 4,510,919 | 4/1985 | Benmussa | 126/263 |
| 4,522,190 | 6/1985 | Kuhn et al. | 126/263 |
| 4,559,921 | 12/1985 | Benmussa | 126/263 |
| 4,736,599 | 4/1988 | Slegel | 62/294 |
| 4,741,324 | 5/1988 | Ina et al. | 126/263 |
| 4,751,119 | 6/1988 | Yukawa | 428/35 |
| 4,753,085 | 6/1988 | Labrousse | 62/294 |
| 4,771,761 | 9/1988 | Doukhan | 126/263 |
| 4,773,389 | 9/1988 | Hamasaki | 126/263 |
| 4,780,117 | 10/1988 | Lahey et al. | 62/4 |
| 4,793,323 * | 12/1988 | Guida et al. | 126/263.08 |
| 4,809,673 | 3/1989 | Charvin | 126/263 |
| 4,819,612 | 4/1989 | Okamoto | 126/263 |
| 4,888,188 * | 12/1989 | Castner, Sr. et al. | 126/263.04 |
| 4,895,135 | 1/1990 | Hamasaki | 126/263 |
| 4,949,702 | 8/1990 | Suzuki | 126/263 |
| 5,035,230 * | 7/1991 | Steidl et al. | 126/263.08 |
| 5,117,809 | 6/1992 | Scaringe | 126/263 |
| 5,205,277 | 4/1993 | Chao-Tsung | 126/262 |
| 5,220,909 | 6/1993 | Pickard | 126/623 |
| 5,248,486 | 9/1993 | Matsuoka et al. | 252/70 |
| 5,255,812 | 10/1993 | Hsu | 220/277 |
| 5,355,869 | 10/1994 | Pickard | 126/263 |
| 5,388,565 | 2/1995 | Ou | 126/263 DC |
| 5,465,707 * | 11/1995 | Fulcher | 126/263.06 |
| 5,477,847 * | 12/1995 | Ueki | 126/263.01 |
| 5,483,949 | 1/1996 | James | 126/263.05 |
| 5,494,598 | 2/1996 | Hughes | 252/70 |
| 5,542,418 | 8/1996 | James | 126/263.09 |
| 5,611,329 * | 3/1997 | Lamensdorf | 126/263.07 |
| 5,626,022 | 5/1997 | Scudder et al. | 62/4 |
| 5,628,304 | 5/1997 | Freiman | 126/263.09 |
| 5,699,902 | 12/1997 | Sperry et al. | 206/219 |
| 5,738,082 * | 4/1998 | Page et al. | 126/263.01 |
| 5,873,221 | 2/1999 | Sperry et al. | 53/472 |
| 5,935,486 * | 8/1999 | Bell et al. | 126/263.01 |

* cited by examiner

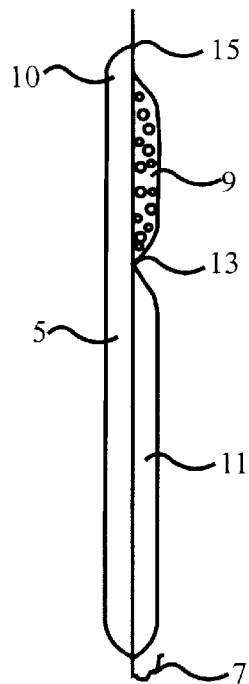
FIG. 2
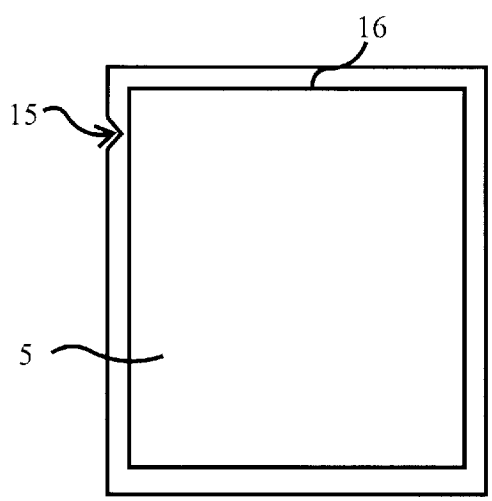
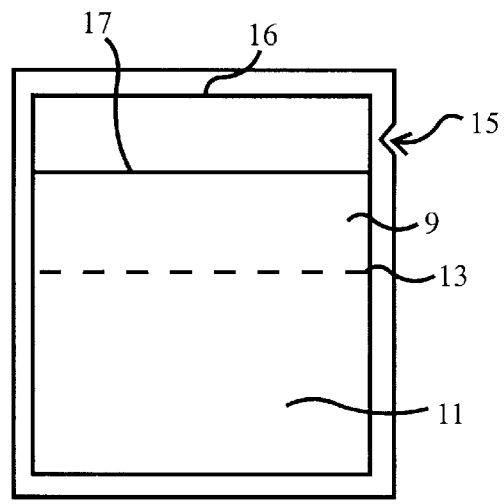
FIG. 3A  FIG. 3B

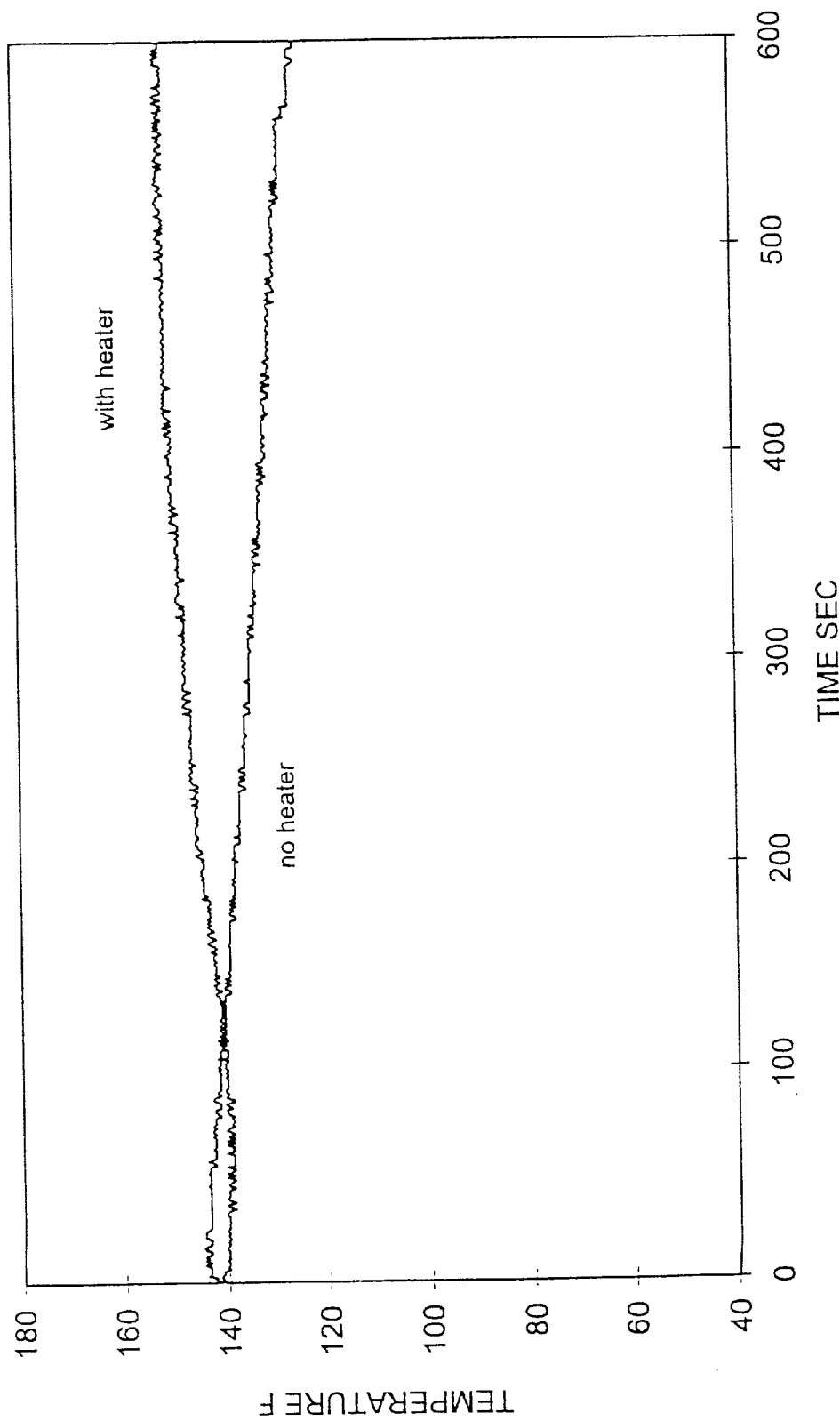

SELF-HEATING FLEXIBLE PACKAGE

BACKGROUND OF THE INVENTION

This invention relates to improved flexible self-heating packages that can be used to heat or warm liquid, semi-liquid, or solid products, or to maintain the temperature of products sold hot, to make them more suitable for their intended use. The self-heating device is one in which a solid or semi-solid heat-producing composition is reacted with an activating liquid, typically water or an aqueous solution, to generate heat. A number of self-heating containers have been reported, but all suffer from disadvantages that decrease their convenience of use or increase the expense for their manufacture.

U.S. Pat. No. 5,628,304 Freiman et al (1997) reports a recyclable self-heating container having two compartments which contain anhydrous calcium chloride and water, respectively. The container is provided with a cutting device that is used to open the water compartment and allow water to contact the anhydrous calcium chloride and release heat.

U.S. Pat. No. 4,773,389 Hamasaki et al. (1988) reports a self-heating foodstuff container having a body with two chambers, a liquid container and a support member. One of the chambers of the body is provided to receive a foodstuff and the second is provided to receive an exothermic reaction agent. The heater is activated by sliding a support member in contact with the body to cause the liquid to be discharged into the second chamber to initiate exothermic reaction.

U.S. Pat. No. 4,793,323 Guida et al. (1988) reports a single-use self-heating container ith a plastic vessel within and attached to an external insulated envelope. Two compartments, an upper and a lower compartment, are provided in the vessel separated by a membrane. The upper compartment contains a solid reactant and the lower contains an activating liquid. The exothermic reaction is initiated by actuating a membrane-breaking member in the liquid compartment. The upper compartment of the vessel optionally contains a temperature control substance which undergoes a phase change between 90° C. and 100° C.

U.S. Pat. No. 4,809,673 Charvin (1989) reports a device for heating food having an upper compartment for receiving food and a lower compartment in which two reagents are separated from each other by one or more watertight partitions. The device is provided with internal radial blades operated from outside of the container by an external control knob to tear the watertight partitions and initiate the exothermic reaction.

U.S. Pat. No. 5,220,909 Pickard et al. (1993) reports a self heating individual meal module includes a tub for holding food to be heated. The tub is welded to a tray and in contact with a pad of an electrolytic-solution-activated exothermic-chemical. The heater also has a pouch containing an electrolytic solution. A pull-tab is provided on the pouch to release the electrolytic solution to activate the chemical pad to generate heat.

U.S. Pat. No. 5,255,812 Hsu (1993) reports a self-heating tin container having a chemical compound for releasing heat upon mixing with a liquid catalyzer. The tin has a cap having an internal compartment containing liquid catalyzer and a pin on its inside surface which is used to pierce the internal compartment and allow liquid catalyzer to contact the chemical compound in the tin. Pressing an elastic top edge of the cap when in place on the tin, causes the pin to pierce the compartment permitting the liquid catalyst to flow into the tin.

U.S. Pat. No. 4,057,047 of Gossett (1977) reports a thermal pack in which heat or cold is generated by contacting water with selected chemicals to generate an exothermic or an endothermic reaction. The thermal pack has three bags, two of which form the outer surface and inner surface of the pack, respectively. The inner of these bags holds the chemicals that will react with water. A third smaller bag containing water is inserted into the inner bag which contains the chemicals. The inner bag is ruptures by hand pressure to release water and activate the chemicals. The smaller inner bag is provided with a marginal seal that facilitates rupture on application of hand pressure.

While a number of self-heating devices have been described, there is a continuing need in the art for devices that are more convenient to use and less expensive to manufacture. Many prior art devices require an additional device element, such as a pin or serrated edge, to bring the heater components into contact to generate heat. This requirement adds to the inconvenience and expense of the device. Other prior art self-heating devices are constructed with one or more rigid pieces that again generally increase cost and add to the bulk of the device.

SUMMARY OF THE INVENTION

The present invention provides heaters and self-heating packages that are more convenient to use and less expensive to manufacture than are currently available. The self-heating package of this invention contains a multi-compartment heater which is activated by application of hand pressure to rupture a frangible seal in the heater.

In one embodiment, the self-heating package has one or more products or product containers in thermal contact with one or more heaters. In preferred packaging embodiments, the heating package has one or more product containers or pouches in thermal contact with one or more heaters. In a specific embodiment, the product container is integrally formed with the heater. Preferred self-heating packages are constructed entirely of flexible packaging materials.

The heater of this invention has a multi-compartment structure having at least one compartment for holding a heat-producing composition and at least one adjacent compartment for holding an activating solution. Adjacent compartments containing activating solution and heat-producing composition are separated by a frangible seal. The heater compartments are formed, at least in part, from a flexible packaging material. Application of sufficient pressure, for example, as applied by hand by squeezing or twisting, on a compartment or compartments of the heater, for example, compression of the activation solution-containing compartment, ruptures the frangible seal, allowing the solution and the heat-producing material to mix and begin heat production. Heaters include those having two adjacent compartments for holding heat-producing composition and activating solution, respectively, separated by a frangible seal.

Once activated the multi-compartment heater pouch can be used to heat a product or to maintain the temperature of a hot or warm product. During use the heater pouch is placed in close proximity to the product to be heated or kept hot. For example, the heater pouch can be placed in direct contact with the product or in contact with a heat-conducting package containing the product. The heater pouch can be placed within thermally insulated packaging that also contains the product. Heaters of this invention can be employed, for example, to maintain a desirable temperature of various take-out foods, including pizza, hamburgers and the like, during transport. The size of the heater is generally adjusted to the size of the product to be heated and the amount of heater components (heat-producing composition and activating solution) in the heater compartments are adjusted to provide the desired temperature for a given heating or warming application. The amount of activating solution provided in the heater is preferably at least enough to react with the amount of heat-producing compound in the heater and optionally is provided in excess to limit the maximum temperature achieved.

An advantage of the heater is that the package can be manufactured from inexpensive, flexible packaging materials appropriate for retaining the liquid activation agent. The packaging material employed preferably can withstand temperatures generated up to about 90° C. in the product pouch, and somewhat higher temperature in the heater pouch (e.g., up to 150° C.). The design is compatible with a variety of heat-producing materials, and is particularly suited for use with heat-producing materials that do not produce a substantial amount of gas in operation, so that the package can remain completely sealed. In this way the user never comes in contact with the heat-producing materials. Addition of an excess amount of activation solution over the amount needed to substantially react with the heat-producing composition can function as a heat sink to minimize generation of steam.

Self-heating packages of this invention have a multi-component heater, as described above, held, attached or bonded to and in thermal contact with a product to be heated or kept hot or warm. Heaters may be held or attached directly in contact with the product or with a thermally conductive product container or pouch which contains the product. Heaters may be held in contact with the product by application of external packaging, such as an overwrapping of thermally insulated flexible packaging material that also functions to hold the heater in place or by application of an adhesive or other bonding agent between the heater and the product or product container. The heater inside the packaging material is activated by hand pressure to release heat and transfer heat to the product. The external packaging or product container can then be opened to extract the heated product.

In a specific embodiment, a self-heating package has a product container or pouch integrally formed with the heater package. For example, the product container can be formed by sealing or otherwise bonding the edges of a sheet of flexible packaging material to a surface of or at the perimeter of the heater. In this package, liquid, semi-liquid or powdered product introduced into the product container is in thermal contact with the heater. Application of hand pressure to the flexible heater compartment(s) ruptures the frangible seal and initiates heat release to heat the product within the container. The product container can be opened, for example as facilitated by appropriate positioning of a tear notch, to remove heated product. The product container may be porous or non-porous.

In another embodiment of the self-heating package, the heater is attached to a porous material, such as a scrim, net or webbing, to form a porous product container. The porous container contains a dry material that is intended to be dissolved or steeped in warm or hot water. The porous material retains the dry material and allows liquid to penetrate into the container. In this embodiment, the package including the heater and attached porous container, once activated, is inserted into a liquid, such as water, to heat the liquid. The product in the porous pouch dissolves or steeps in the heated liquid to add a desirable flavor or other attribute to the liquid. The porous container can contain, for example, a dry beverage (tea or coffee) or flavoring agent that is intended for addition to or immersion in hot water for consumption.

In yet another embodiment of the self-heating package, the heater is attached to an absorbent or coated substrate or an encapsulated material where the product to be heated is absorbed or coated on the substrate or is the encapsulated material. In this embodiment, heating results in release of the absorbed or coated product from the substrate or release of encapsulated product.

The heaters and self-heating packages are designed for use with a heat-producing material or materials activated by addition of a liquid, preferably water or an aqueous solution, to the heat-producing compositions. A variety of heat-producing compositions are useful in this invention. In particular, heat-producing compositions described in PCT/US97/12846, U.S. Pat. No. 5,935,486 and U.S. patent application Ser. No. 09/351,821, filed Jul. 12, 1999, all of which are incorporated by reference herein in their entirety to the extent that they are not inconsistent with the disclosure herein. The heat-producing material or materials may be in the form of a pad, powder, granules, or a combination of the above. The heat-producing materials are preferably solid or semi-solid. Heat-producing compositions can comprise an active heat-producing component in combination with an inert material. The inert material does not react with activating solution to generate a substantial amount of heat and can serve to moderate or control heat release on activation. Heat-producing compositions can include, among others, $CaO$, $MgCl_2$ and $Na_2SO_4$. In one preferred embodiment, the active heat-producing components area mixture of an acidic anhydride or an acidic salt with a basic anhydride and a basic salt. Acidic anhydrides include phosphorous pentoxide. Acidic salts include aluminum chloride and magnesium chloride. Basic anhydrides include calcium oxide Preferred active heat-producing components are calcium oxide alone, a combination of phosphorous pentoxide and calcium oxide or a combination of magnesium chloride and calcium oxide. Inert materials which typically represent from about 1% to about 30% by weight of the heat-producing composition include among others surfactants, oils, waxes, and natural or synthetic polymeric solids. Preferred heat-producing compositions produce substantially no gases on activation. Preferred heat-producing compositions are water-free.

BRIEF DESCRIPTION OF THE DRAWINGS

FIG. 2 is a side view in more detail of the heating package of FIG. 1C having a two-compartment heater bonded or attached to a product pouch.

FIGS. 3A and B are front and back views of the heater package of FIG. 2. The product container is illustrated on the front side of the package and the two-compartment heater is illustrated on the back side of the package.

FIG. 8 is a graph of temperature change as a function of time of a food item in a product container with and without inclusion of an activated heater of this invention in the container.

DETAILED DESCRIPTION OF THE INVENTION

The invention relates to heaters in which heat is generated by exothermic reaction of active ingredients. The heaters generate heat without application of external heat energy. Preferred active ingredients are a liquid activating solution (preferably water or an aqueous solution) and a heat-producing solid. In the sealed heaters of this invention liquid is brought into contact with the heat-producing material to generate heat. The heaters are formed as multi-compartment elements where the compartments are preferably formed from flexible packaging materials. Activating solution and heat-producing compositions are held in separate compartments in the heater. Compartments are separated by frangible seals that can be readily ruptured by application of hand pressure to the flexible heater compartments. The heater components generate heat on activation. Dependent upon the application of the heater a variable amount of heat may be desired. Heaters may be used to heat cold items or maintain the temperature of warm or hot items. In the latter application, the heater need not provide enough heat to raise the temperature of the product heated, but only enough heat to slow cooling of the product. The heater is provided in a sealed package to avoid contact of heater components with the surroundings and to maintain the activity of the heat-producing material. Heaters of this invention can be used alone or in a self-heating package.

Self-heating packages combine a heater with a product or product container. The heater is in thermal contact with the product or product container in the package. The heater is activated in the package, by application of hand pressure to rupture one or more frangible seals that cause activation of the heater. The heater components are retained in a compartment separate from the product. After the product is heated inside the package a portion of the packaging can be opened to remove the product for use.

The invention is further illustrated by reference to the drawings in which the same numbers are used to indicate similar features.

Figure 1A:
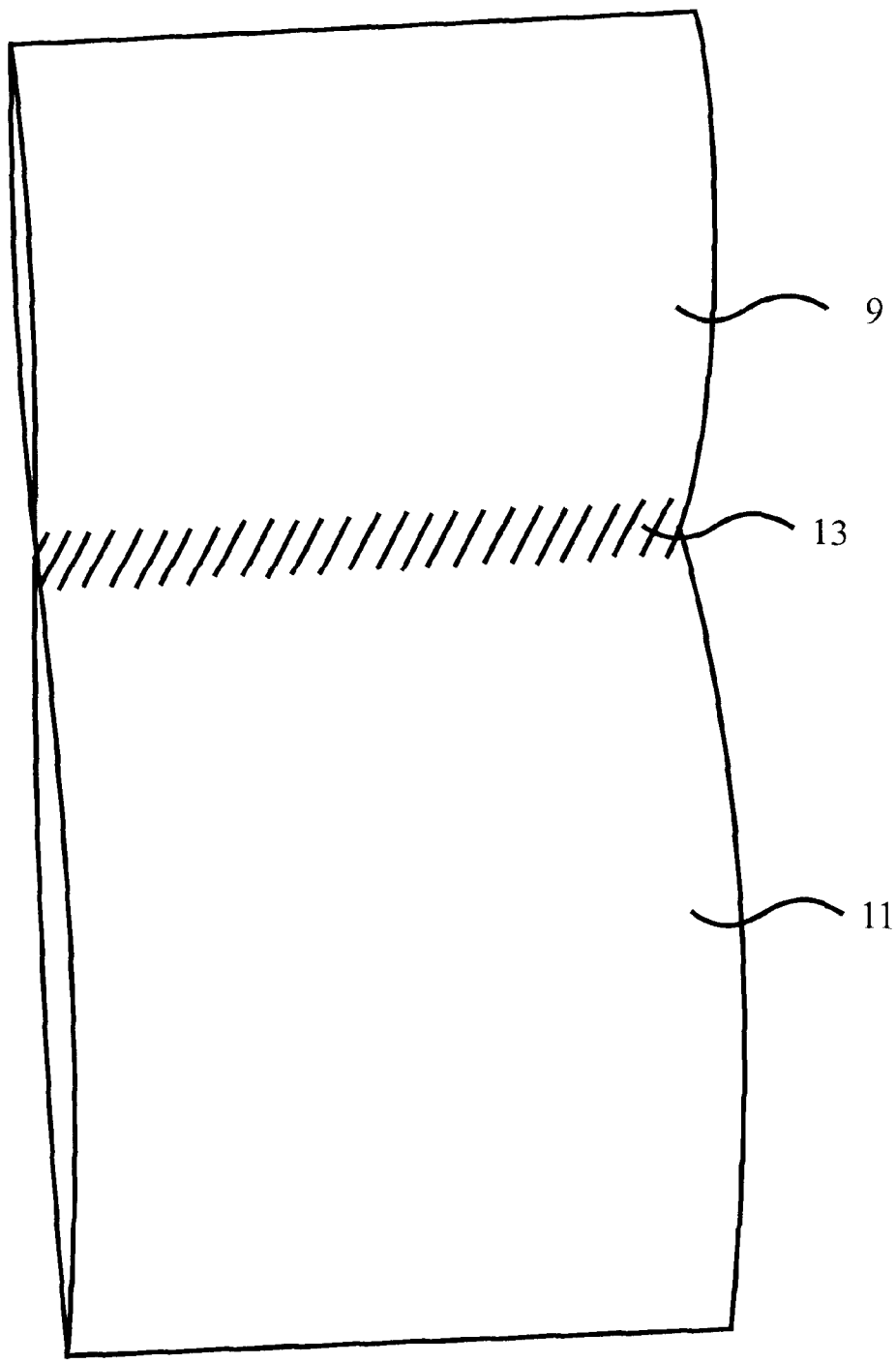
FIG. 1A is a schematic illustration of a two-compartment heater of this invention.
Figure 1F:
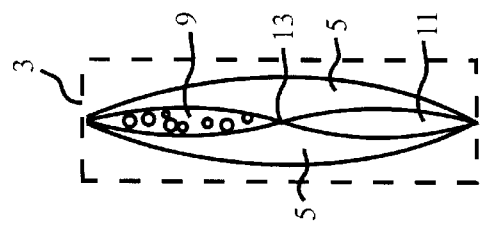
FIGS. 1B–1P are drawings that illustrate, in side view, various configurations of one or more heaters of FIG. 1A in combination with one or more product container or pouch. The self-heating packages of FIGS. 1A–1P are preferably entirely constructed of flexible materials.
Figure 1E:
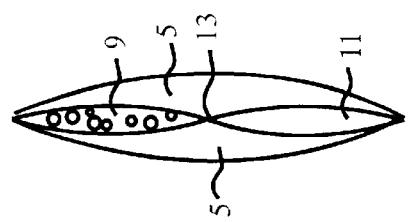
Figure 1D:
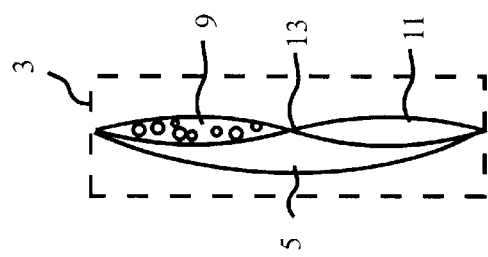

FIG. 1A illustrates an exemplary two-compartment heater 1 of this invention constructed from flexible materials. The heater has compartment 9 which contains activating solution (preferably water or an aqueous solution) and compartment 11 which contains a heat-producing composition which is typically a solid. The two compartments are separated by a frangible seal 13 that prevents contact of the heat-producing composition and the activating solution until pressure is applied to rupture the seal. The seal is constructed to be ruptured by application of pressure by hand by twisting or squeezing the flexible heater. For example, the seal can be ruptured by application of hand pressure to a flexible wall of a heater compartment. FIG. 1B illustrates a side view of a heater of FIG. 1A. The frangible seal is preferably sufficiently large to allow efficient mixing of components.

Figure 1C:
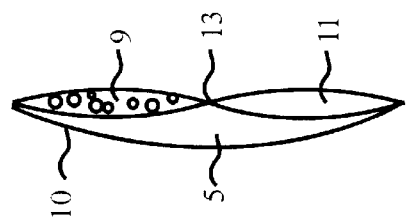
Figure 1B:
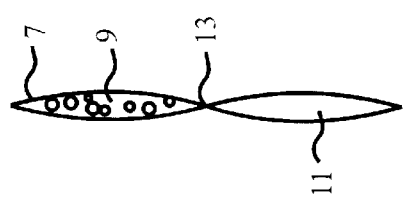
Figure 1K:
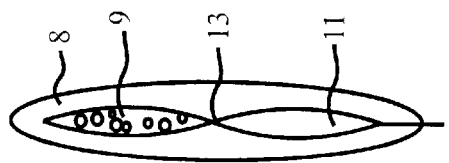
Figure 1J:
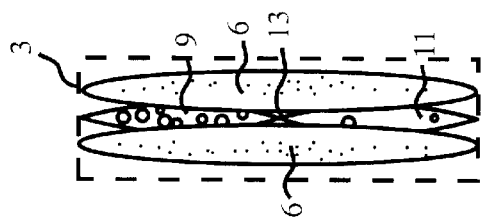
Figure 1I:
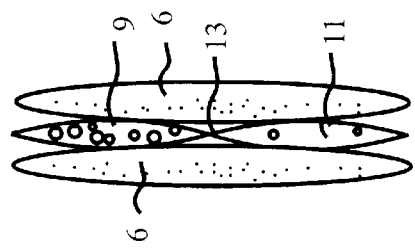
Figure 1H:
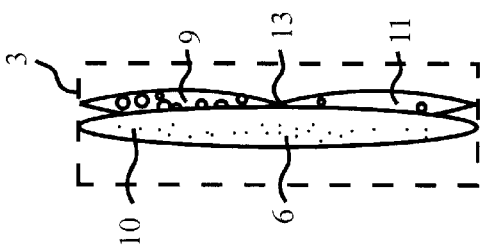
Figure 1G:
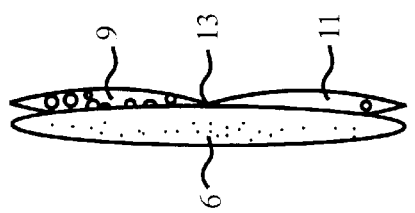
Figure 1P:
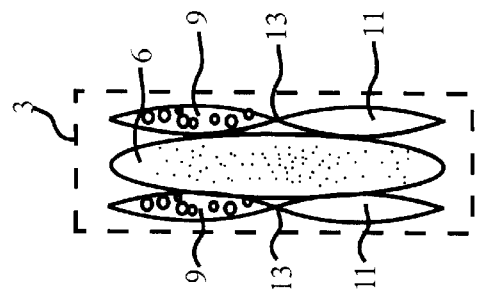
Figure 1O:
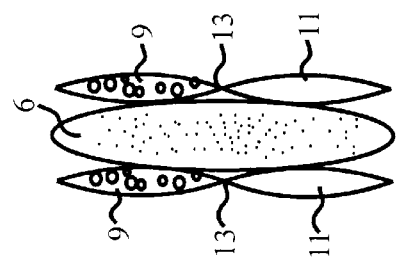
Figure 1N:
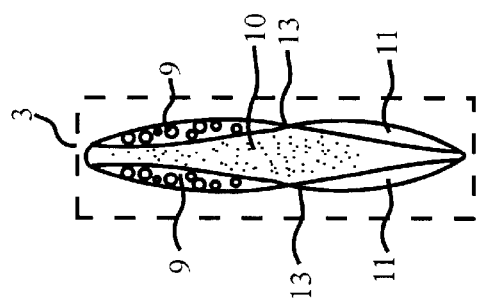
Figure 1M:
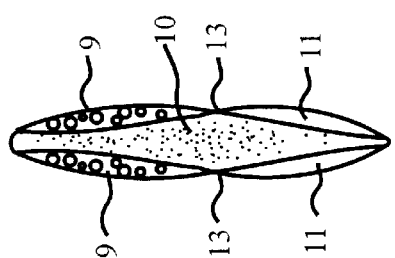
Figure 1L:
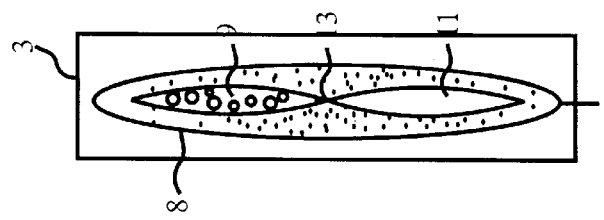

Various configurations of a self-heating package which combine one or more heaters with one or more product containers are shown in FIGS. 1C–1P (in side view). The package may be produced in several configurations that facilitate heat transport from the heat-producing material to the product to be heated The heater package (FIG. 1B) may be roughly rectangular in shape, with a thickness that is less than either the length or the width with the two compartments illustrated in FIG. 1A for receiving activating solution and heat-producing composition 9 and 1, respectively. The material to be heated can be attached to one or both sides of the heater package. Attachment can be effected by adhesive or mechanical means, if the product to be heated consists of a single piece or multiple large pieces. If the product to be heated consists of a liquid, semi-liquid, or powder, it may be contained within a pouch 5 formed of a single layer of flexible packaging material that is bonded to the heater, as shown in FIGS. 1C–F, where the product pouch is sealed to the heater so that a surface of the heater forms at least a portion of the product pouch. Alternatively, the product to be heated may be contained within two or more layers of packaging material, preferably flexible packaging material, which form a pouch or container 6 separate from the heater pouch. The separate pouch 6 may be attached, e.g., adhesively or mechanically to the heater (FIGS. 1G–1J). In yet another embodiment, the product to be heated may be contained within a flexible container or pouch 8 that completely or partially surrounds the heater (FIGS. 1K–1L). This embodiment has the particular advantage of enhancing heat transfer because the heater is surrounded by product to be heated. Two product pouches may be formed at or attached to opposite sides of the heater (FIGS. 1E, 1F, 1I and 1J). Two or more heaters can be formed at or attached to or adjacent to the product side of the product pouch (FIGS. 1M–1P). Pouch 12 in FIGS. 1M and 1N is integrally formed between two heaters. In all configurations illustrated, a thermally insulating material may be provided, either as part of the packaging material forming the various compartments of the heating package or as a separate layer, to retard transfer of heat from any or all parts of the total package to the surroundings. Various insulation materials can be employed including flexible paper or plastic structures having enclosed air pockets to slow heat transfer. Preferably no insulation is positioned between the heater and the product pouch. For example, an outside layer (overwrap 3) of insulating material may serve to retard heat transfer to the surroundings (FIGS. 1D, IF, 1H, 1J, 1L, 1N and 1P).

More detailed schematic drawings of a self-heating product of this invention, of the general design shown as FIG. 1C, where the product is a liquid, semi-liquid or powder solid, are shown in FIG. 2 and FIGS. 3A and 3B. The combined heater/product pouch package of FIG. 2 10 has a product pouch 5 made of a flexible material. The product pouch is bonded to and in thermal contact with a multiple compartment heater pouch 7 having at least one compartment 9 for holding activating solution, preferably water, and at least one pouch 11 containing heat-producing composition. The two compartments 9 and 11 of the heater are separated by a frangible seal 13 which can be readily ruptured on application of hand pressure (i.e., by squeezing or twisting). Product can be removed from the pouch 5 via a tear notch 15 opening. FIG. 3A gives a front side (product side) view of the pouch illustrating the position of tear notch 15 near the top of the product package sealed with the heater package by peripheral seal 16. FIG. 3B gives a back side view of the heater compartment. Heater material is contained in the lower pouch 11 and the activating solution is contained in the upper pouch 9. The pouch containing activating solution 9 is sealed at the top (opposite the frangible seal 13) with a non-frangible seal 17 that will withstand pressure applied by hand.

FIGS. 2, 3A and 3B also illustrate another aspect of this invention, the arrangement of heater and product such that it is convenient to open the product container while leaving the heater container unopened. This is accomplished by having the product container extend past the heater container in one direction, as illustrated in FIG. 3B, and providing means to open the product container, e.g., a tear notch, along a line that does not extend into the heater part of the self-heating product.

The self-heating package illustrated in FIGS. 3A and B can be formed for example by heat sealing a front sheet of packaging material to one surface of a multi-compartment heater.

The heaters in FIGS. 1A, 2, 3A and 3B illustrate heaters with two compartments: one for activating solution and one for heat-producing composition. Heaters of this invention can contain a plurality of compartments for either activating solution or heat-producing composition. At least one compartment for activating solution is positioned adjacent to at least one compartment containing heat-producing solution with the adjacent compartments separated by a frangible seal as described above. When the seal is ruptured the activating solution and heat-producing composition in adjacent compartments come into contact activating the heat-producing composition. One compartment containing heat-producing composition may be positioned adjacent to more than one compartment containing activating solution to facilitate mixing after rupture of the frangible seal.

Figure 4:
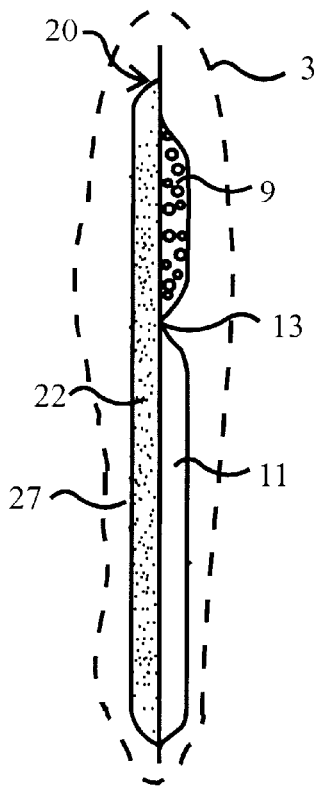
FIG. 4 is a schematic illustration, in side view, of an alternative self-heating package in which the product container or pouch is at least partially porous. The product pouch contains dry material that dissolves in heated water or from which flavoring is extracted into heated water.

FIG. 4 illustrates another self-heating package of this invention in which the combined heater compartments are attached to a porous pouch 20 containing a dry material 22, such as instant or ground coffee, tea, or a beverage flavoring agent. The pouch contents do not require heating, but they are used with hot water to prepare edible beverages or soups. The dry ingredients are intended to be dissolved in or steeped in hot water. The heater is activated by rupture of the frangible seal 13 with hand pressure and the entire package is inserted with attached product scrim 20 into a vessel containing water. A layer of insulation 23 is optionally positioned between the heater and the pouch 20. The heater is used to heat water in the vessel. During and after the water is heated the dry product is steeped or dissolved in the warm or hot water. The water is heated sufficiently for use as a hot or warm beverage. FIG. 4 illustrates a porous pouch (made of porous material 27, e.g., paper or plastic, e.g., tea-bag paper or scrim) containing dry material 22 for dissolving or steeping in hot or warm water bonded to a two compartment heater pouch 7 having a compartment 9 for holding activating solution, preferably water, and a pouch containing heater material 11. The two compartments 9 and 11 of the heater are separated by a frangible seal 13 which can be readily ruptured on application of hand pressure (e.g., by squeezing and or twisting). A layer of insulation 23 is optionally positioned between the porous pouch and the heater compartments. In this embodiment, the heater compartments are not insulated from the surroundings, since the heater on activation is intended to heat water or other liquid into which it is inserted. The heater is activated by breaking the frangible seal between the two heater compartments and the entire package is inserted into a vessel containing water or other liquid. Heat released from the heater heats the water and the dry ingredients in the porous pouch interact with the heated water to extract or dissolve flavorings into the water. The dry ingredients in the porous pouch can include: natural materials, e.g., mixtures of herbs, coffee and teas (dried or instant), flavoring agents, concentrated beverages (soup or bouillon), encapsulated beverages or flavorings and freeze-dried beverages or flavorings. The dry ingredients can also be mixed with sugar, salt, fruit zest or other seasonings. The porous pouch 20 can be formed from a variety of materials with various pore sizes adapted to the desired application. Porous produced containers can be formed from paper, plastic or related materials. Preferred materials are those that can be readily sealed or bonded to heaters of this invention.

The heater package of FIG. 4 can also contain dried or powdered medicinals, and herbs, leaves, plant oils and the like having medicinal effect. The package can be used to provide heated medicinal solutions and suspensions for ingestion. Other heating package configurations of this invention, e.g., as in FIG. 2, can be used to provide heated salves or creams for application to the skin, and for heated solutions for inhalation.

In general the heater packages of this invention can be applied for generation of heated liquids, creams, salves, lotions, solutions, and like media that are edible, used in medicinal applications, used in personal care products, used for cleaning, such as dry or moist towels, towelettes and wipes, and a wide variety of other applications.

In a particular embodiment, heater packages of this invention include those in which towels, towelettes or wipes (the product) is wrapped around a heater, as illustrated in FIG. 1K or 1L, and the combination optionally encased in an appropriate outer package. Application of hand pressure to the enclosed heater releases heat to warm the towel, towelette or wipe.

The packaging material is an important component of this invention. The packaging material may be either transparent or opaque. A lower water vapor transmission rate (WVTR) will increase the shelf life of the product. The packaging material may be capable of forming a heat seal of variable strength, nonfrangible and frangible seals, such that when pressure is applied to the liquid compartment, the frangible seal between the liquid compartment and the heater material compartment 13 opens to admit the liquid to the heater material compartment, but the nonfrangible perimeter seal 16 and any nonfrangible top seal 17 do not open. A heat seal strength of about 3 pounds per inch is desirable for the frangible seal, while a heat seal strength of about 12 to 15 pounds per inch is desirable for the perimeter seal and any top seal to avoid perimeter seal breakdown when hand pressure is applied. Both the frangible seal 13, the top seal 17, and the perimeter seal 16 may be formed in a single operation by adjusting the temperature, pressure, and time of application of the bars used to form the heat seal. Those skilled in the art will recognize that additional means may be employed as necessary to increase the strength of the perimeter seal, such as using a serrated, rather than a plain seal or a wider seal.

A preferred flexible multiple layer packaging material for forming the heater comprises a water vapor barrier layer and an inner layer that functions to form variable strength heat seals. The inner layer may be provided only where seals are intended to be formed. The packaging material must have sufficient mechanical strength to withstand typical manufacturing processes, transport, storage and handling of such items. Mechanical strength may be provided by the water vapor barrier layer or by addition of a resin layer, e.g., an olefinic resin layer, to provide additional mechanical strength. A polyethylene layer is useful for providing sufficient mechanical strength. The packaging material can further comprise an outer protective resin layer, that preferably is compatible for receiving printing and/or graphic images. A polyester resin is suitable for this outer layer.

An exemplary flexible composite packaging material for use with heaters and self-heating packages comprises (1) a thin layer of aluminum foil as a water vapor transmission barrier (e.g., a 0.0003 inch layer of aluminum foil), and (2) a heat sealable inner layer of an ethylene ionomer, such as a 3 mil thick layer of SURLYN™ (DuPont). This composite packaging material can also have an outer layer of 48 gauge polyester which will receive graphics and printing. Further, a layer of 0.7 mil polyethylene can be provided between the outer layer and the foil to provide for sufficient mechanical strength and to protect the foil from damage. Several commercial packaging materials can provide the properties useful for heaters of this invention and be capable of forming variable strength seals. One particularly useful material is available under the trade name Vari-seal (Cadillac Products).

The aluminum foil layer can be replaced, for example, with other materials that provide a water vapor transmission barrier, such as ethylene-vinyl alcohol copolymer. Alternative heat sealable layers include linear low-density polyethylene.

Films for use in heaters and packages of this invention should be compatible with the heater components (activating solution and heat-producing composition) such that the film is not detrimentally affected by those components. The flexible film and other packaging materials must be compatible for use with food, beverages, pharmaceuticals or personal care products. The materials used must be approved, if required, by the pertinent regulatory agencies for use in a given application. Many flexible materials may be used in this invention. Suitable materials can be selected by one of ordinary skill in the art in view of the disclosures herein and in view of the type of application with the aid of a standard reference, such as "The Wiley Encyclopedia of Packaging Technology" (M. Bakker, ed., NY, Wiley, 1986).

Seals may be made as is known in the art by applying pressure from a heated bar, controlling the temperature of the bar, the pressure and the length of time that the pressure is applied to form a seal of desired strength. Seals of heaters and self-heating packages specifically exemplified herein were formed with a Vertrod heat-sealer. A seal strength of about 3 lbs/inch is desirable for frangible seals and a seal strength of about 12–15 lbs/inches is desirable for nonfrangible, perimeter seals. Heater packages and self-heating packages of this invention can be filled and sealed in a single operation using any conventional equipment, including vertical and horizontal form/fill/seal machinery.

Those of ordinary skill in the art will appreciate that other materials known in the art are functionally equivalent to and can be used to replace packaging materials specifically described herein. Information on polymer film with appropriate properties for use in the heaters and self-heating packages of this invention may be found in the "Concise Polymeric Materials Encyclopedia" (J. C. Salamone, ed.; NY, CRC Press, 1999).

A variety of heat-producing compositions can be employed in the practice of this invention. Preferred heat-producing compositions are those that are activated by the addition of a liquid, preferably water or an aqueous solution, to the heat-producing compositions. Heat-producing compositions can include inexpensive materials such as lime (CaO), sodium sulfate and magnesium chloride and mixtures thereof. Particularly useful heat-producing compositions are described in PCT/US97/12846, U.S. Pat. No. 5,935,486 and U.S. patent application Ser. No. 09/351,821, filed Jul. 12, 1999, all of which are incorporated by reference herein in their entirety to the extent that they are not inconsistent with the disclosure herein. Heat-producing compositions can comprise an active beat-producing component in combination with an inert material. The inert material does not react with activating solution to generate a substantial amount of heat and can serve to moderate or control heat release on activation. The inert material may serve to inhibit access of the activating solution to the active heat-producing components. In preferred embodiments, the active beat-producing components are a mixture of an acidic anhydride or an acidic salt with a basic anhydride and a basic salt. Acidic anhydrides include phosphorous pentoxide. Acidic salts include aluminum chloride. Basic anhydrides include calcium oxide. Heat-producing compositions include a combination of phosphorous pentoxide and calcium oxide and a combination of magnesium chloride and calcium oxide. Specific heat-producing compositions include: calcium oxide alone, about 10%–90% by weight calcium oxide with the balance being phosphorous pentoxide or about 25%–50% by weight magnesium chloride with the balance being calcium oxide.

Inert materials can most generally represent from about 1% to about 30% by weight of the heat-producing composition. More preferably the inert material represents up to about 20 weight % of the heat-producing composition. In specific embodiments heat-producing compositions contain from about 10 to 20 weight % of inert materials. Inert materials include among others surfactants, oils, waxes, natural or synthetic polymeric solids and mixtures and mixtures thereof. Inert materials can include mixtures of surfactants and oil. Surfactants of particular interest for this application include organic phosphate esters, oil-soluble surfactants, polyethoxylated alcohol, and polyamide succinimide. Preferred surfactants include among others Actrafos 216 (Trademark), stearic acid, dicetylphosphate, Paranox 100 and Brij 30 (Trademark). Preferred oils include among others aliphatic hydrocarbons, vegetable oils and mineral oil.

Preferred heat-producing compositions contain a mixture of active components, such as CaO or combinations of CaO with $P_2O_5$ or $MgCl_2$ in combination with inert material that can be a mixture of surfactant, oil, and/or wax. Heat-producing compositions can be prepared for example, as pads, pellets or powders. In preferred embodiments of this invention, the heat-producing composition is formed into pellets, preferably ranging in size from about mesh 6 to about mesh 16. The use of larger size pellets tends to decrease the rate of heat generation on activation. The rate of heat generation in the heaters of this invention can be controlled by selection of the type of active ingredients, the amount of inert material included and the physical form of the composition.

Preferred heat-producing compositions produce substantially no gases on activation. Preferred heat-producing compositions are water-free. Preferably heat-producing compositions are selected and the amount used adjusted to provide a desired amount of heat transfer in a given application dependent upon the product to be heated and the packaging of the product.

The heat-producing compositions may be in the form of a pad, powder, pellets, granules, or a combination of the above. The heat-producing materials are preferably solid or semi-solid.

The type and amount of heat-producing composition and activating solution in the heater compartments are predetermined to obtain desired heat release appropriate for the product to be heated and to minimize the risk of rupture of the heater.

Figure 5:
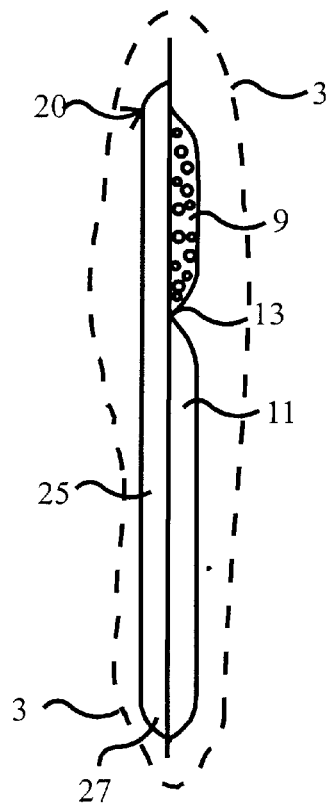
FIG. 5 is a schematic illustration, in side view, of another alternative self-heating package in which the product container is porous and intended to contain a product material that releases scent on heating.

A further aspect of this invention shown in FIG. 5 is a package design that enables convenient heating of a liquid product that is volatile or contains a volatile component, so as to evaporate or volatilize the volatile material into the atmosphere. Examples of such products include insect repellent, room deodorizer, or other desirable scents. The volatile liquid or mixture containing it may be absorbed onto an absorbent material 25 such as paper, vermiculite or ground corn cobs. The absorbent material is attached to the heater, for example by adhesive or mechanical means and may be held within a porous container 20. In particular, if the absorbent material is a powder or granular solid, it may be contained and held in proximity to the heater by a porous material 27 (such as paper or a nonwoven scrim material) having pores chosen so as to retain the absorbent and allow the volatile material to pass through. As will be obvious to those skilled in the art, a self-heating product of this design may be produced with means to prevent the evaporation of the volatile materials until desired, either by covering the part of the product containing the volatile materials with an additional layer of impermeable flexible packaging film, or by containing the entire product 30 in a bag or pouch of impermeable flexible packaging film.

The volatile component may be encapsulated in a material, e.g., a wax, that melts on heating. Encapsulated product may be coated or absorbed on to the absorbent material. The absorbed material may be treated, for example, by soaking in a solution containing the product and removing the solvent.

The packaging systems and methods of this invention can also be applied to packaging of personal care products (e.g., oils and lotions for application to the skin or hair). The packaging system of this invention is particularly amenable to single-use or single-serving size applications.

The packaging systems and methods of this invention can also be applied to packaging of food items which are more palatable when heated and particularly to those items that are thick semi-liquid viscous products at room temperature, but become less viscous on heating (i.e., sauces for use on ice cream, heated salad dressings).

Figure 6:
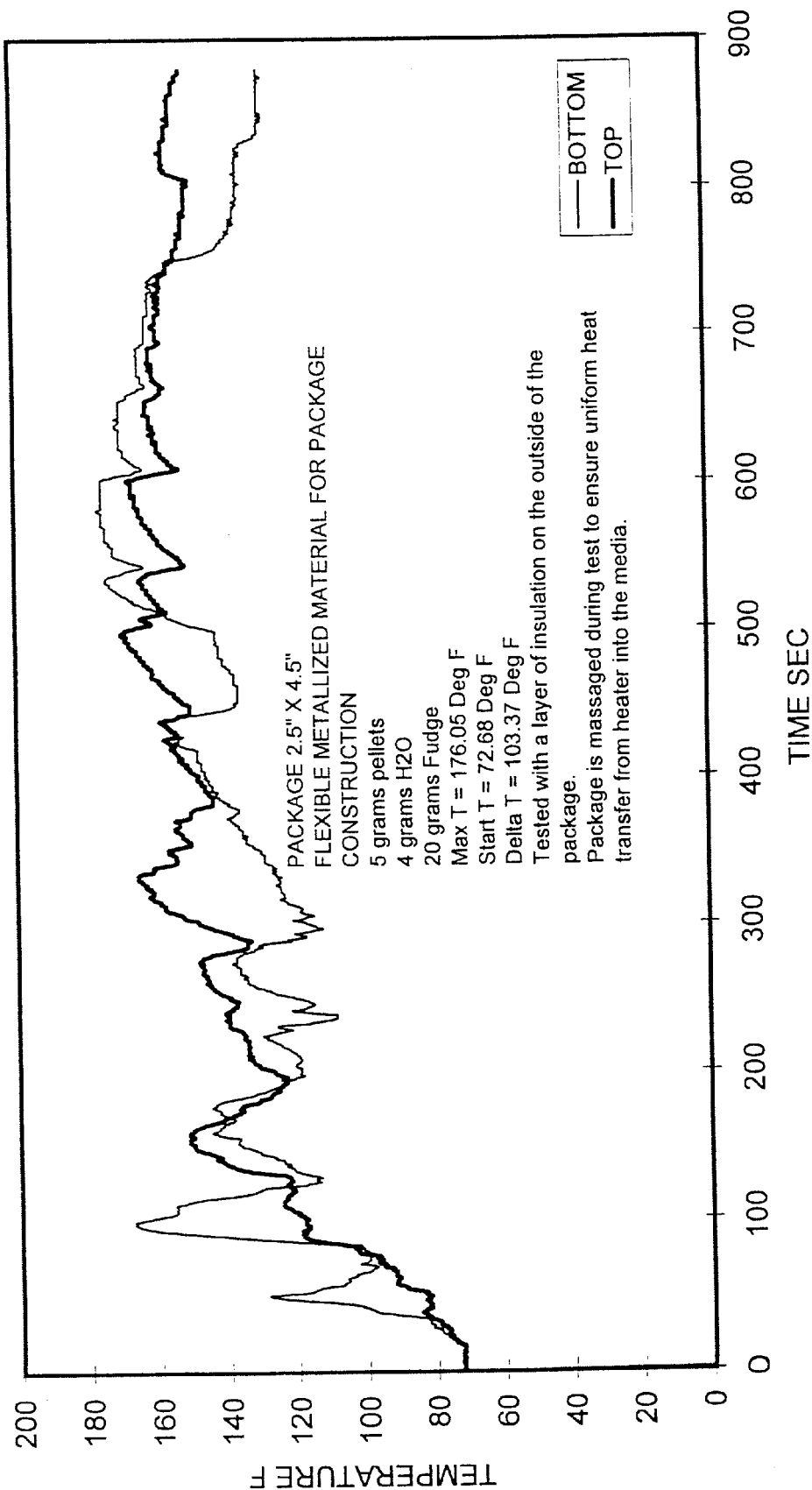
FIG. 6 is a graph of product temperature as a function of time after heater activation by rupture of a frangible seal in a self-heating package as illustrated in FIG. C. The product is fudge sauce and product temperature is measured at the bottom (dots) and top (squares) of the product pouch.
Figure 7:
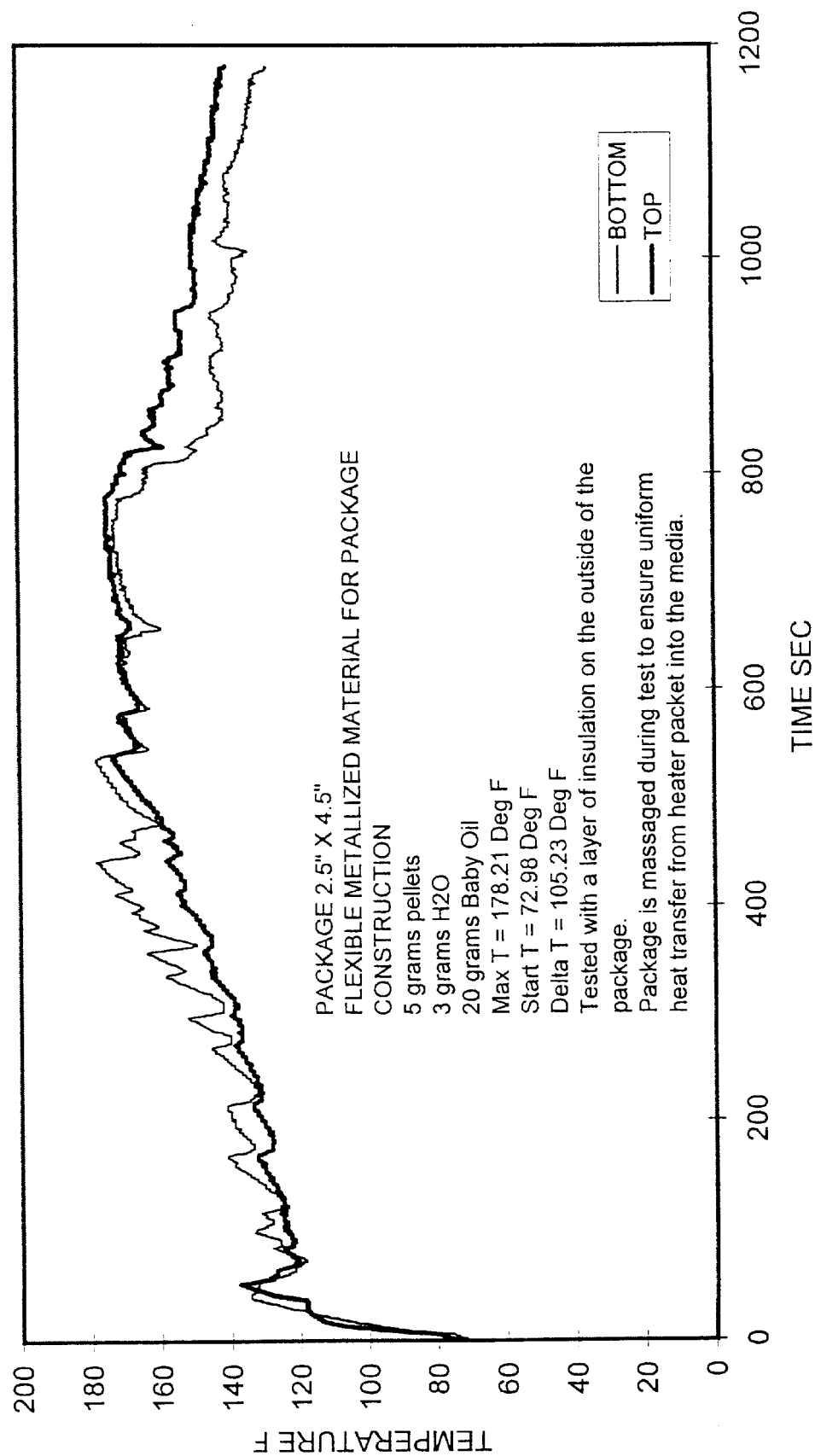
FIG. 7 is a graph of product temperature as a function of time after heater activation by rupture of a frangible seal in a self-heating package as illustrated in FIG. 1C. The product is baby oil and product temperature is measured at the bottom (dots) and top (squares) of the product pouch.

The performance of two self-heating packages of design illustrated in FIGS. 2, 3A and 3B is illustrated in the graphs of FIG. 6 and FIG. 7. From these data it is clear that a small amount (ca. 5 g) of heater material activated with ca. 3–4 g water is sufficient to heat about 20 g of oil or fudge sauce. The heater material used in both experiments was the same: a mixture of 86.6% by weight of the active ingredient: a 1:1 weight ratio mixture of CaO: $P_2O_5$ and 13.4% by weight of an inert material: a mixture of 74% by weight mineral oil and 26% by weight of the surfactant Actrafos 216 (TM), an organic phosphate ester. The packaging for the self-heating packages tested comprised an outer layer of 48 gauge polyester, a layer of about 0.7 mil polyethylene, an 0.0003 inch layer of aluminum foil and a 3 mil layer of an ionomer (Surlyn, Trademark) to form the variable strength heat seal. Temperatures ranging from about 120–180° F. can be attained within about 3 minutes or less. A temperature above ambient can be maintained for over 20 minutes.

Many food and beverage products are sold hot, and are more desirable if kept hot until consumed. During the time that passes between purchase and consumption, e.g. during transport to another location, the food or beverage can cool off and become less desirable. The flexible heater of this invention can be inserted into or used in conjunction with various hot food or beverage containers to keep these products hot or warm, i.e., to slow the decrease in temperature of the product. In use the package is squeezed or twisted to rupture the frangible seal, allowing the heater material and water or aqueous solution for activation to mix and begin the process that produces heat. The heater is then placed or held in proximity to the product to be kept hot, until the product is consumed. It is desirable that such a self-heating package reach a temperature hotter than the minimum desirable temperature of the product, but less than the boiling point of water. In this way heat transfer to keep the product hot is feasible, but the self-heating package does not generate any significant amount of steam or internal pressure. The self-heating package can thereby remain sealed, so that no solid, liquid or vapor from the heater comes into contact with the product or the consumer.

In an exemplary embodiment using the heater in take-out food applications, a quarter-pound cheeseburger in a box of thin cardboard, as is commonly used in fast food businesses, can be kept hot by using a multi-compartment flexible heater. The size of the heater is chosen to fit inside the bottom of the food container and preferably to substantially conform in size to the dimensions of the container to maximize the contact area available for heat transfer from the heater to the product. Various sizes and shapes of food and beverage containers are generally employed in food service. Heaters of this invention can generally be tailored to fit any of such product containers to provide efficient heat-transfer to the product.

A two-compartment heater was constructed as a composite structure with an outer layer of 48 gauge polyester, a 0.0003 inch layer of aluminum foil as a water vapor barrier, a layer of about 0.7 mil polyethylene between the outer layer and the foil, and an inner 3 mil layer of an ionomer to form a variable strength heat seal. One compartment contained 4 g of a heat-producing composition that was a mixture of 86.6% by weight of the active ingredient: a 1:1 weight ratio mixture of CaO: $P_2O_5$ and 13.4% by weight of an inert material: a mixture of 74% by weight mineral oil and 26% by weight of the surfactant Actrafos 216 (TM), an organic phosphate ester. The second compartment contains 4 grams of water. This self-heating package is 3.5×3.5 inches square, divided into two compartments by a frangible seal. On activation the mixture in the heater package becomes hot, but the package remains sealed. In a comparison test in which a heater is placed against the bottom of a cardboard box containing a cheeseburger in one case, compared to the same size cheeseburger without a heater in the second case, the time-temperature profiles shown in FIG. 8 are obtained. In this case the cheeseburger is actually heated: its temperature increases from 141° F. to 152° F. over ten minutes with the heater, where the same size cheeseburger without the heater cools from 144 to 125° F. over the same time. In practice it is only necessary that use of the self-heating package results in the product cooling significantly less than it would without the heater, and thereby remaining more attractive to consumers.

It is an important feature of this invention that the heat producing composition (and the residue after activation) can remain sealed before, during and after use and does not contact the product. This minimizes any negative effect that either part of the heater system may have on the heated product. Further, the use of a sealed heater minimizes risk of potentially harmful effects of the heater components on users (e.g., toxic or allergic reactions). In a specific package design, to ensure that the heater package remains sealed, any of the following changes may be made singly or in combination: The amount of heat-producing composition may be decreased (e.g., by increasing the proportion of inert materials or by increasing the particle size of the heater materials, or both), or the amount of water or aqueous solution used for activation may be increased to provide an additional heat sink.

As an additional feature of this invention, means may be provided to give the user an indication that the heater system has not remained sealed. Such means may include a dye added to either the heater material or the liquid used to activate the heater, or both. When the integrity of the heater system is compromised, the dye will give a visual signal that product quality may also be compromised. The heater packaging may be transparent or have a transparent window to allow possible undesired release of dye to be observed. Alternatively, a substance with a strong, objectionable taste or odor may be added to the heater system. When the integrity of the heater system is compromised, the objectionable taste or odor will signal that product quality may also be compromised and discourage inappropriate use.

The heater or self-heating packages of this invention may also be provided with some means to indicate that the heater or the product in the package have reached a selected temperature that indicates for example that the product is at a temperature suitable for consumption or use. For example, liquid crystal materials that change color with increasing temperature can be used for such an indicator. Alternatively, dyes that become colorless when hot, to reveal a legend or graphic that was previously concealed by the dye when colored, can also be used for such an indicator.

Several heater or heating packages can be combined to conveniently give a large quantity of the desired hot product. Combining several smaller packages rather than one large package may be advantageous in certain applications to provide more efficient and more rapid heat-transfer to product.

The outer packaging of the multi-compartment heaters of this invention are intended to remain sealed to prevent release of heater components or residues to the surroundings. In the event that excessive pressures occur that might rupture the heater package, an optional feature of this invention is provision of a vent and means to control the position of venting such that any steam or gases vented from the heater are directed in a harmless direction, and to insure that the excess pressure does not cause the package to rupture. A selective vent can be provided by selective placement of a weaker seal region in the perimeter seal of the heater. The vent seal would be stronger than the frangible seal so that it would not rupture by application of hand pressure, but weaker than the perimeter seal.

Methods for forming frangible seals and nonfrangible perimeter seals are well-known in the art and can be readily adapted for use in the self-heated products of this invention. U.S. Pat. Nos. 5,699,902 and 5,873,322 provide details and references to methods for frangible seal formation that are applicable to making the packages of this invention. All of the heater/product container combinations of FIGS. 1A–1P can be readily prepared using methods known in the art in view of the disclosures herein. Methods are known in the art for bonding sheets of flexible materials, e.g., heat sealing of plastics or related materials, to form durable seals needed to form heater compartments and product compartments. Similarly, art-known methods can be employed to bond or attach porous materials to flexible packaging materials to form porous product compartments.

By using flexible packaging and a frangible seal that is produced as an integral part of the packaging and in the same operation as the package is formed, self-heating products of this invention may be made at lower cost, and are lighter and smaller than comparable products using prior art.

All of the references cited herein are incorporated by reference herein in their entirety to the extent that they are not inconsistent with the disclosures herein.

We claim:

1. A self-heating package for heating a product which comprises
   (a) a heater comprising:
     a first non-porous compartment containing a predetermined amount of activating solution, the first compartment having a flexible wall;
       a second non-porous compartment adjacent the first compartment containing a predetermined amount of a heat-producing composition the second compartment having a flexible wall; and
       a frangible seal formed between and separating said first and second compartments that can be ruptured by pressure applied by hand to allow activating solution in the first compartment to contact the heat-producing composition in the second compartment thereby generating heat; and
   (b) a flexible product container wherein a surface of the heater forms at least a portion of the product container and wherein the heater when activated transfers heat to the product or to the product in the container.

2. The self-heating package of claim 1 having a plurality of first compartments containing activating solution and a plurality of second compartments containing a heat-producing composition.

3. The self-heating package of claim 1 wherein the activating solution is water.

4. The self-beating package of claim 1 wherein said heat-producing composition comprises calcium oxide.

5. The self-heating package of claim 1 wherein the heat-producing composition comprises an inert material selected from the group consisting of surfactants, oils, and waxes.

6. The self-healing package of claim 5 wherein the inert material is a surfactant.

7. The self-heating package of claim 5 wherein the inert material is a mixture of surfactant and oil.

8. The self-heating package of claim 5 wherein the inert material does not undergo a phase change between 90° C. and 100° C.

9. The self-heating package of claim 1 in which the heater is formed by perimeter heat scaling of two sheets of flexible packaging material.

10. The self-heating package of claim 9 wherein the perimeter heat seal has a strength of about 12–15 lb/inch and the frangible seal has a strength of about 3 lbs/inch.

11. A method for maintaining the temperature of a hot or warm food or beverage product contained in a product container which comprises the steps of:
   (a) providing a self-heating package of claim 1 wherein the product is a hot or warm food or beverage item; and
   (b) activating the heater in the self-heating package to generate beat by applying hand pressure to the first or second compartment to rupture the frangible seal to allow activating solution in the first compartment to contact the heat-producing composition in the second compartment thereby generating heat to maintain the temperature of the product.

12. The self-heating package of claim 1 wherein the product container is nonporous.

13. The self-heating package of claim 1 wherein the product container is porous.

14. The self-heating package of claim 1 having a plurality of product containers in thermal contact with the heater.

15. The self-heating package of claim 1 having a plurality of heaters in contact with the product or product container.

16. The self-heating package of claim 1 wherein the product surrounds the heater.

17. The self-heating package of claim 1 wherein the product container is provided with a tear notch to facilitate removal of heated product from the product container.

18. The self-heating package of claim 1 wherein the product container is an absorbent substrate with product absorbed thereon.

19. The self-heating package of claim 1 wherein the product container is a coated substrate with product coated thereon.

20. The self-heating package of claim 1 wherein the product is encapsulated.

21. The self-heating package of claim 1 wherein the product is a scent absorbed on an absorbent substrate.

22. The self-heating package of claim 1 wherein the product is a dry or moist towel, towellette or wipe which surrounds the heater.

23. The self-heating package of claim 1 wherein the product container is a porous scrim and the product is selected from the group of mixtures of herbs, coffee, tea, flavoring agents, concentrated beverages, encapsulated beverages and freeze-dried beverages or flavorings.

24. The self-heating package of claim 1 wherein the heat producing composition consists essentially of a mixture of phosphorous pentoxide and calcium oxide or a mixture of magnesium chloride and calcium oxide.

25. The self-heating package of claim 1 which comprises a flexible product container which surrounds the heater.

26. The self-heating package of claim 1 comprising a plurality of product containers wherein a surface of the heater forms at least a portion of each product container.

27. The self-heating package of claim 1 wherein the heat-producing composition comprises an inert material and is formed into pellets or granules.

28. The self-heating package of claim 27 wherein the heat-producing composition is formed into pellets ranging in size from about mesh 6 to about mesh 16.

29. The self-heating package of claim 27 wherein the inert material is a surfactant.

30. The self-heating package of claim 27 wherein the inert material is a mixture of surfactant and oil.

31. A method for heating a product which comprises:
 (a) providing a self-heating package of claim 1; and
 (b) activating the heater of the self-heating package by applying hand pressure to the first or second compartment to rupture the frangible seal to allow activating solution in the first compartment to contact heat-producing composition in the second compartment thereby generating heat to heat the product.

* * * * *

UNITED STATES PATENT AND TRADEMARK OFFICE
CERTIFICATE OF CORRECTION

PATENT NO. : 6,289,889 B1
DATED : September 18, 2001
INVENTOR(S) : Bell et al.

It is certified that error appears in the above-identified patent and that said Letters Patent is hereby corrected as shown below:

Column 1,
Line 3, please replace "TBE" with -- THE --.
Line 29, please replace "ith" with -- with --.

Column 2,
Line 7, please replace "ruptures" with -- ruptured --.

Column 4,
Line 8, please replace "self-beating" with -- self-heating --.
Line 18, please replace "beat-producing" with -- heat-producing --.
Line 28, please replace "area" with -- are a --.
Line 32, please insert a period after "oxide".

Column 5,
Line 3, please replace "FIG. C." with -- FIG. 1C --.

Column 10,
Lines 9 and 15, please replace "beat-producing" with -- heat-producing --.

Column 14,
Line 39, please replace "self-beating" with -- self-heating --.
Line 64, please replace "beat" with -- heat --.

Signed and Sealed this

Twenty-sixth Day of March, 2002

Attest:

*Attesting Officer*

JAMES E. ROGAN
*Director of the United States Patent and Trademark Office*